(12) United States Patent
Voss et al.

(10) Patent No.: US 7,442,820 B1
(45) Date of Patent: Oct. 28, 2008

(54) PROCESS FOR THE PREPARATION OF PLATINUM ACETYLACETONATO COMPLEXES

(75) Inventors: Steffen Voss, Garden Grove, CA (US); Dongshui Zeng, Yorba Linda, CA (US); Stephen Jeffery, Huntington Beach, CA (US); Kevin King, Torrance, CA (US)

(73) Assignee: W.C. Heraeus GmbH, Hanau (DE)

( * ) Notice: Subject to any disclaimer, the term of this patent is extended or adjusted under 35 U.S.C. 154(b) by 0 days.

(21) Appl. No.: 12/020,092

(22) Filed: Jan. 25, 2008

(51) Int. Cl.
*C07F 15/00* (2006.01)
(52) U.S. Cl. .................................... 556/136
(58) Field of Classification Search ................. 556/136
See application file for complete search history.

(56) References Cited

U.S. PATENT DOCUMENTS

2008/0103322 A1* 5/2008 Fehn ......................... 556/136

OTHER PUBLICATIONS

Guo et al., Chem. Mater., vol. 10, No. 2, pp. 531-538 (1998).*
Wang et al., Inorg. Chem., vol. 40, No. 23, pp. 6000-6003 (2001).*

* cited by examiner

*Primary Examiner*—P. Nazario Gonzalez
(74) *Attorney, Agent, or Firm*—Norris, Mclaughlin & Marcus, P.A.

(57) ABSTRACT

Preparation of halogenide-free Platinum(II)acetylacetonate [Pt(acac)$_2$] Platinum(II) hexafluoroacetylacetonate [Pt(hfac)$_2$], Platinum(II) trifluoroacetylacetonate [Pt(tfac)$_2$] or Platinum(II)-alkylsubstituted acetylacetonates by the reaction of a halogen free platinum (IV) oxo- or hydroxo-compound, such as $PtO_2 \cdot nH_2O$ (n being an integer from 1 to 4) or $H_2Pt(OH)_6$ or $Na_2Pt(OH)_6$ or $K_2Pt(OH)_6$, with a reducing agent in aqueous solution in the presence of a stoichiometric or higher amount of acetylacetone (acac), potassium acetylacetoante (Kacac) sodium acetylacetonate (Naacac), hexafluoroacetylacetone (hfac), trifluoroacetylacetone (tfac) or alkyl substituted acetylacetones or their salts and an $H^+$ donor.

14 Claims, No Drawings

PROCESS FOR THE PREPARATION OF PLATINUM ACETYLACETONATO COMPLEXES

The invention relates to a novel process for the production of platinum acetylacetonato complexes, especially Pt(II) acetylacetonate [Pt(acac)$_2$].

Using the Werner method (Ber. 1901, 2584), which was later verified by Grinberg and Chapurskii [Zhur. Neorg. Khim 4, 314-18 (1959)], K$_2$PtCl$_4$ is dissolved in hot water and mixed with six equivalents of KOH. Once the reddish solution turns yellow, eight equivalents of acetylacetone (Hacac) are added. This mixture is stirred rapidly, heated to 50° C., and maintained at this temperature for 1-1.5 h until crude Pt(acac)$_2$ precipitates. The solution is cooled and the pale yellow crude product collected by filtration. More KOH and Hacac are added and the solution is again heated to 50° C. for 1 h until another crop of product has precipitated. Multiple iterations are carried out until no more precipitate forms. Pure product can be obtained from recrystallization in benzene. Yields range from 25-35%. The major disadvantages of this process are low yield, use of excess Hacac ligand and employment of benzene as recrystallization solvent.

The Okeya-Kawaguchi method calls for dissolution of K$_2$PtCl$_4$ in 1 N HClO$_4$. This solution is mixed with mercury (II)oxide and silver perchlorate in excess perchloric acid. The aquated solution of Pt$^{2+}$ stabilized by perchloric acid is filtered to remove KClO$_4$, HgCl$_2$, and AgCl. The [Pt(H$_2$O)$_4$]$^{2+}$ solution is treated with Na(acac) which forms a creamy-yellow solid. Once all the ligand has been added, the solution is pH adjusted to 4.5 and stirred for 20 h. This solid is collected by filtration, washed with DI water, and dried over silica gel in vacuo to give the crude product. The solid is dissolved in CH$_2$Cl$_2$, filtered, and chromatographed over silica gel. The solvent is removed in vacuo leaving behind a pure yellow product which is recrystallized from benzene in 75% yield. The drawbacks to this process are use of the dangerous and toxic reagents mercury, perchlorates, benzene and CH$_2$Cl$_2$. In addition, the yield, which is much higher than that of the Werner method, is not economical on an industrial scale and is complicated by the presence of heavy metals.

The object of the invention is to address the following features which caused problems in the methods found in the chemical literature: yield, safety of chemical reagents used, recovery of Pt from the mother liquor, and economical use of ligand.

Surprisingly, improvements are achieved regarding these features when halogenide-free Platinum(II)acetylacetonate [Pt(acac)$_2$] or Platinum(II) hexafluoroacetylacetonate [Pt(hfac)$_2$] or Platinum(II) trifluoroacetylacetonate [Pt(tfac)$_2$] or Platinum(II)-alkylsubstituted acetylacetonates are prepared in the following manner:

I. A halogen free platinum (IV) oxo- or hydroxo-compound, such as PtO$_2$ n H$_2$O (n being an integer from 1 to 4) or H$_2$Pt(OH)$_6$ or Na$_2$Pt(OH)$_6$ or K$_2$Pt(OH)$_6$, is reacted with II. a reducing agent III. in aqueous solution in the presence of IV. a stoichiometric or higher amount of acetylacetone (acac), potassium acetylacetoante (Kacac) sodium acetylacetonate (Naacac), hexafluoroacetylacetone (hfac), trifluoroacetylacetone (tfac) or alkyl substituted acetylacetones or their salts V. and a H$^+$ donor.

It is advantageous when the temperature is kept under 85° C. during reaction. Diluted aqueous solutions are preferred, the total amount of water present in the reaction mixture being e.g. 30 to 150 molar equivalents based on platinum.

The protons (H$^+$) may be provided by suitable organic or inorganic acids such as carboxylic acids or mineral acids. Suitable carboxylic acids are acetic acid or citric acid. Preferred acids are mineral acids, especially H$_2$SO$_4$, HNO$_3$, or H$_3$PO$_4$. It is advantageous to have about ½ molar equivalent—based on Pt—of protons available.

Suitable reducing agents are known in the art. Examples are formic acid, formic acid derivatives, oxalic acid, ascorbic acid, hydrogen, sugars, formaldehyde, hydrazine, hydrazinium salts, alcohols, and hydrogen peroxide.

Formic acid is preferably used as a dilute solution.

Preferably no reagents, which can exacerbate the recovery of Pt from the mother liquors in recycling, nor additional metals nor excess organics are present in the process.

In a preferred embodiment of the invention the following steps are performed:

A One molar equivalent of platinum (IV) oxide as H$_2$Pt(OH)$_6$ is suspended as a slurry in water.

B To this slurry, about 30 to 100 molar equivalents of water, slight a molar excess of acac (2,4-pentanedione) and about 0.5 mol H$_2$SO$_4$ are added.

C1 The mixture is heated to 50-85° C., preferably while stirring.

C2 One molar equivalent of optionally diluted formic acid is added, preferably portionwise or dropwise, D The mixture is kept at 85° C. until its color has a changed from yellow to green or black. Out-gassing of carbon dioxide is observed.

E The suspension is filtered and the solid precipitate is washed and recrystallized to give a bright yellow product.

The present process brings about the following advantages:

Yields of over 90% based on platinum may be achieved.

The reaction does not require an inert atmosphere, i.e. it can be carried out under ambient atmospheric conditions.

Over-reduction of the Pt(IV) starting material to Pt(0) by formic acid is a typical problem; however, by using a highly aqueous system and applying of stringent temperature controls, the addition of formic acid is cushioned and over-reduction lessened.

After harvesting the product, the mother liquor is mainly aqueous which makes recovery of the precious metal easier.

The chemical literature cites [PtCl$_x$(acac)$_y$]$^n$ species that are formed in solution along with the desired product. By comparison, the product obtained by the present process is higher in purity and yield due to the absence of chlorides because halogen containing reactants are avoided.

The aqueous solvent system makes later recovery of any unconverted platinum easy.

No heavy metal contaminants such as mercury are present.

The reaction may be performed as a one pot synthesis. However, higher yields are obtained when formic acid is diluted separately and added in a controlled fashion.

The mother liquor, which is mainly water, and the washings may be further processed by methods known in the art such as treatment with hydrazine, or more commonly with aqua regia followed by borohydride reduction. The fact that only a slight excess of organic ligand is employed allows for a reduced amount of organics in any reclaimed platinum; therefore, recovery of platinum from waste streams is facile. Firstly, higher yields mean less over-reduction to produce finely divided Pt in the product which is extremely pyrophoric. Secondly, less acetylacetone in the system also means there is less fuel to feed the potential for fire, thus reducing the potential for accident or injury.

Furthermore, one will immediately realize that an increase in overall yield results in more product and consequently less Pt sent to the refinery.

The following example will further illustrate the invention. Percentages are based on weight unless otherwise indicated.

EXAMPLE $H_2Pt(OH)_6$, "platinum oxide", is obtained as a slurry in water and assayed by direct ignition for percent Pt. After properly suspending the Pt starting material, to this slurry are added 75 molar equivalents of deionized water, 2.5 molar equivalents of Hacac, and 0.5 molar equivalents of $H_2SO_4$ based on Pt. After the addition of all reagents, the reactor is sealed and an oil bubbler attached which is vented to a fume hood. This mixture is vigorously stirred and heated to 85° C. While the mixture is heating, an addition funnel connected to the reactor is loaded with one equivalent of $HCO_2H$, and then diluted to approximately 0.5 L with DI water. When the reactor has reached temperature, the $HCO_2H$ solution is added drop-wise at a rate of 1-2 drops/s over a period of no less than 4 h. This typically equates to an addition rate of 100 mL/h. Once all of the $HCO_2H$ has been added, the temperature is held for no less than 3 hours. On occasion, the reaction has been allowed to go overnight to which there were no adverse affects on yield.

As time progresses, the reaction emits copious amounts of $CO_2$ gas and the slurried oxide changes in color from light yellow to grayish-green or black. At the conclusion of the reaction, the suspension is filtered in air and collected in a Büchner funnel revealing a light amber mother liquor. The crude product is washed with DI water until sulfate free. Continued water washings result in a lighter colored crude product in which yellow flecks of product are often observed. The crude product is dried in vacuo under an Ar atmosphere. The crude product is recrystallized from organic solvents and activated carbon. The suspension is heated for 20 mins, filtered, and the solvent removed in vacuo leaving behind a bright yellow solid.

The elemental analyses of C and H was within 0.2% of the theoretical values with C, 30.53% and H: 3.59%.

The invention claimed is:

1. A process for the production of halogenide-free Platinum(II)acetylacetonate [Pt(acac)$_2$] or
Platinum(II) hexafluoroacetylacetonate [Pt(hfac)$_2$] or
Platinum(II) trifluoroacetylacetonate [Pt(tfac)$_2$] or
Platinum(II)-alkylsubstituted acetylacetonate,
wherein
  I. a halogen free platinum (IV) oxo- or hydroxo-compound is reacted with
  II. a reducing agent
  III. in aqueous solution in the presence of
  IV. a stoichiometric or higher amount based on platinum (IV) of acetylacetone (acac), hexafluoroacetylacetone (hfac), trifluoroacetylacetone (tfac) or alkyl substituted acetylacetonate or their salts and
  V. a H$^+$ donor.

2. A process for the production of chloride-free Platinum(II)acetylacetonate [Pt(acac)$_2$] or
Platinum(II) hexafluoroacetylacetonate [Pt(hfac)$_2$] or
Platinum(II) trifluoroacetylacetonate [Pt(tfac)$_2$] or
Platinum(II)-alkylsubstituted acetylacetonate
according to claim 1.

3. A process according to claim 1 wherein the halogenide free platinum (IV) oxo- or hydroxo-compound is PtO$_2$.n H$_2$O or H$_2$Pt(OH)$_6$,
  n being an integer from 1 to 4.

4. A process according to claim 1, wherein the reaction temperature is kept under 85° C.

5. A process according to claim 2, wherein the reaction temperature is kept under 85° C.

6. A process according to claim 1 wherein 30 to 150 molar equivalents of water are present in the reaction mixture.

7. A process according to claim 1 wherein H$^+$ is provided by a mineral or organic acid as donor.

8. A process according to claim 7 wherein the mineral acid is one of the following H$_2$SO$_4$, HNO$_3$, and H$_3$PO$_4$.

9. A process according to claim 1 wherein the reducing agent is selected from the group consisting of formic acid, formic acid derivatives, oxalic acid, hydrazine, hydrazine derivatives, hydrazinium salts, hydrogen peroxide, and alcohols.

10. A process according to claim 9 wherein the reducing agent is used as a dilute aqueous solution.

11. A process according to claim 1 wherein
  the product is isolated as a solid precipitate, washed and recrystallized.

12. A process according to claim 11 wherein the product is recrystallized from an organic solvent, optionally in the presence of activated carbon.

13. A process according to claim 1 wherein the reaction is carried out in air.

14. A process according to claim 1 wherein no reagents, which can exacerbate the recovery of Pt from the mother liquors in recycling nor additional metals nor excess organics are present.

\* \* \* \* \*